(12) United States Patent
Raju

(10) Patent No.: US 11,857,440 B1
(45) Date of Patent: Jan. 2, 2024

(54) INTEGRATED Z AND WALLSTENT

(71) Applicant: Seshadri Raju, Jackson, MS (US)

(72) Inventor: Seshadri Raju, Jackson, MS (US)

(*) Notice: Subject to any disclaimer, the term of this patent is extended or adjusted under 35 U.S.C. 154(b) by 0 days.

(21) Appl. No.: 17/305,099

(22) Filed: Jun. 30, 2021

(51) Int. Cl.
| | |
|---|---|
| *A61F 2/82* | (2013.01) |
| *A61F 2/852* | (2013.01) |
| *A61F 2/86* | (2013.01) |
| *A61F 2/90* | (2013.01) |
| *A61F 2/848* | (2013.01) |

(52) U.S. Cl.
CPC .......... *A61F 2/90* (2013.01); *A61F 2/82* (2013.01); *A61F 2/848* (2013.01); *A61F 2/86* (2013.01); *A61F 2230/0028* (2013.01); *A61F 2230/0069* (2013.01); *A61F 2250/001* (2013.01)

(58) Field of Classification Search
CPC .... A61F 2/90; A61F 2/86; A61F 2/848; A61F 2/04; A61F 2/06; A61F 2/07; A61F 2/82; A61F 2250/001; A61F 2230/0028; A61F 2230/0069; A61F 2002/828; A61F 2002/30322
See application file for complete search history.

(56) References Cited

U.S. PATENT DOCUMENTS

| | | | |
|---|---|---|---|
| 4,655,771 A | 4/1987 | Wallsten | |
| 5,282,824 A | 2/1994 | Gianturco | |
| 5,755,781 A | 5/1998 | Jayaraman | |
| 6,585,758 B1* | 7/2003 | Chouinard | D04C 1/06 623/1.16 |
| 9,034,028 B2* | 5/2015 | Lorenzo | A61F 2/82 623/1.15 |
| 2004/0116999 A1* | 6/2004 | Ledergerber | A61F 2/07 623/1.42 |
| 2007/0179590 A1* | 8/2007 | Lu | D04C 1/06 623/1.53 |
| 2011/0264186 A1* | 10/2011 | Berglung | A61F 2/86 623/1.11 |
| 2018/0055665 A1* | 3/2018 | Gorochow | A61F 2/852 |

OTHER PUBLICATIONS

Raju, Seshadri, et al. A Modification of Iliac Vein Stent Technique, Journal of Vascular Surgery, Aug. 2014, vol. 28, No. 6, Elsevier.

* cited by examiner

*Primary Examiner* — Dinah Baria
(74) *Attorney, Agent, or Firm* — Intellectual Property Consulting, LLC; Bernard F. Meroney

(57) ABSTRACT

One embodiment of the invention incudes a single cylinder zigzag strut Z stent cylinder fixedly joined to a braided stent such that a portion of the joined Z stent cylinder extends beyond the termination end of the braided wire stent. The Z stent cylinder can have a larger in diameter than the braided stent when expanded.

6 Claims, 2 Drawing Sheets

INTEGRATED Z AND WALLSTENT

FIELD OF INVENTION

The invention relates to stents used in the venous system; in particular, stents for use near the iliac-caval junction.

BACKGROUND OF THE INVENTION

Iliac vein stenting has been employed to address a wide spectrum of advanced chronic venous disease. Braided stents are commonly used in the venous system. A braided stent uses small diameter metal wire such as 80-180 μm diameter wire that is braided into a mesh-like configuration. One common braided stent used in venous stenting is the Wallstent™ 10 from Boston Scientific. It is braided with fine wires that are spiral wound into a mesh braided pattern into a closed cell. See FIG. 2. The individual wire braid strands 11 are Elgiloy alloy, a Cobalt-Chromium-Nickel-Molybdenum alloy. They are spiral wound into a closed cell cylindrical mesh, such as 1.7 mm 2 mesh, and form a self-expanding stent, as described in U.S. Pat. No. 4,655,771, incorporated by reference. This design imparts necessary flexibility to its structure, but stent length will vary with constrained diameter, reducing deployment accuracy. When compressed near the ends, the cylindrical form transforms into a cone with narrowed ostia. Constriction of the stent diameter by as much as 20-30% can occur due to recoil in some tight lesions despite adequate lesion predilation, resulting in unpredictable stent length after deployment. This can result in local stent migration. These stent "end effects" are particularly common when treating lesions at or near the iliac-caval junction where primary and post thrombotic lesions occur frequently.

At the iliac-caval junction, compressive forces are often present; this causes stent placement difficulties, particularly when attempting to position the stent "precisely" at the junction to avoid stent encroachment into the vena cava proper. The inventor has advocated extension of the Wallstent for 3-5 cm into the inferior vena cava to avoid these placement difficulties. However, "jailing" (or reduction of flow) of the contralateral iliac flow caused by a closed cell Wallstent protruding into the inferior vena cava can be a concern with this technique.

To reduce jailing by the Wallstent, the inventor proposed placing a Gianturco Z stent by Cook Medical, atop the Wallstent, with the Z stent protruding into the interior vena cava. The Z stent 20 used was composed of two stacked sequential cylinders, 21 each cylinder formed from a stainless wire 22 in a zigzag closed cylinder configuration (the struts are commonly referred to as Z struts) where the two cylinders are mated together and held into a cylindrical shape by a series of three synthetic sutures 23, one on each end and one at the join of the two cylinders. The wine in the cylinder is continuous. See FIG. 2. The Z stent 20 is a semi-rigid open cell self-expanding stent as more particularly described in U.S. Pat. No. 5,282,824 incorporated by reference. The Z stent Z shaped struts or wire typically stainless steel or nitinol, self-expanding open cell stents with large interstices spaces between the struts, where the struts are thicker the wire use in braided stents. The thick struts imparts rigidity to the Z stent, as the Z strut itself is not very flexible. Usually, two cylinders are stacked together with sutures as shown in FIG. 1.

In this technique, Wallstents 10, such as an 18-mm diameter stent, are deployed with the upper end preferably starting at the iliac-caval junction and ending preferably in the common femoral vein below the inguinal ligament. The standard double cylinder Z stent 20 is then deployed with the topmost suture removed, The Z stent 20 is deployed in the interior of the Wallstent 10 such that the upper Z struts extend about 1.4-2 cm into the inferior vena cava and the remainder of the Z stent 20 (including the remainder of the upper Z stent struts) are deployed within the confines of the topmost Wallstent 10. This overlap provides additional radial strength at the iliac-caval junction and improves fixation against the iliac-caval choke point. See FIG. 3. The widely spaced Z struts at the upper end allow outflow from the contralateral iliac vein without constraint, greatly reducing the possibility of jailing. It is preferred to oversize the Z stent relative to the Wallstent, otherwise embolization of the Z stent is a risk.

This technique is not without issues. For instance, if the Wallstent is extended too far into the inferior vena cava, jailing of contralateral iliac vein flow can still occur despite placement of the Z stent on top of the Wallstent stack. This requires close attention to placement of the Wallstent 10 and Z stents 20; in effect adjusting the overlap of the Z stent such that only the exposed (i.e., exterior to the Wallstent) upper portion of the first cylinder's Z 20 extends into the interior vena cava. This technique was described in "Modification of the Iliac Vein Stent Technique", by Raju, Ward, Jr. Kirk. *Annuals of Vascular Surgery*, Vol 28. No 6, Elsevier, 2014, incorporated by reference. A better stent design is needed to overcome placement difficulties of the two stents.

SUMMARY OF THE INVENTION

One embodiment of the invention incudes a cylinder Z stent zigzag strut stent cylinder fixedly joined to a braided stent cylinder such that a portion of the joined Z stent cylinder extends beyond the termination end of the braided wire stent cylinder. The Z stent cylinder can have a larger diameter than the braided stent when expanded.

DESCRIPTION OF THE PREFERRED EMBODIMENTS OF THE INVENTION

Figure 2:
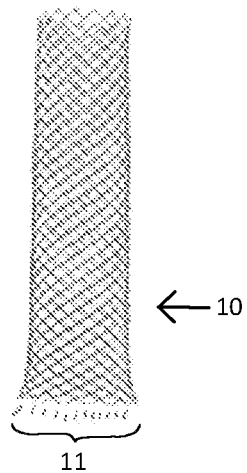
FIG. 2 is a front prospective view of a Wallstent after expansion.
Figure 1:
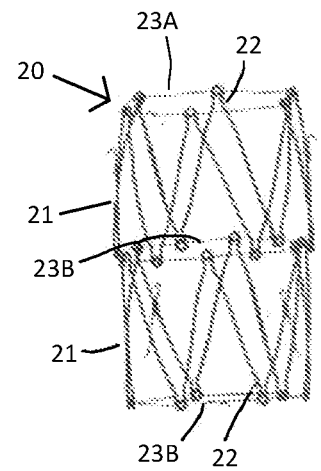
FIG. 1 is a front perspective view of a Z stent after expansion

To avoid placement issues present in deploying two stents at different locations at different times, the proposed invention is to fixedly attach or alternatively, integrally attach, a single cylinder zigzag wire stent, or a modified Boston Scientific Z stent, or other modified Z stents, all hereinafter all referred to as a Z stent 10 (preferably 20 mm diameter when expanded) into a braided stent 30, such as a Wallstent 20 (preferably 18 mm diameter when expanded). The combination 50 can be created with other braided stents and is not limited to the Wallstent 20. The diameter sizes are exemplary to the specific location described below and not limiting. However, it is preferred that the Z stent wire thickness be thicker than the braided stent or Wallstent. The Z type stent to be attached is preferably a single cylinder 2 (see FIG. 3) of length 6-10 cm, where one or both of the upper and lower sutures connecting the Z struts which constrain stent expansion can be eliminated if desired. The single cylinder Z stent may also be joined exterior to or interior to the braided stent or Wallstent, with overlap between the two stents. Interior attachment is preferred, to allow the braided stent to act as an exterior sleeve restricting the full expansion of the Z-stent cylinder 21 and to provide additional resistance to compressibility. The Z stent join with the braided stent or Wallstent can also be coterminous or end to end, provided a secure joint can be achieved. This version is not preferred for extension into the vena cava as the Z stent cylinder 21 expansion is not restrained except at the join.

Attachment of the two stents can be a weld, such as a laser weld, or a flexible metal braided suture type of attachment; or, a synthetic fiber suture, such as nylon, polyester, PVDF and polypropylene can be used to couple the two stents, as long as the stents are fixedly joined when the join is complete (cannot be separated in the intended use). Alternatively, the upper ends of the braided stent or Wallstent strands can be grouped in subsets where each subset can be wound around corresponding individual Z struts at the desired locations and then welded together, or a subset of the braided stent or Wallstent upper ends can be welded to corresponding Z struts. Attention should be paid to the selected weld locations or other join type locations to ensure the entire combined joined structure can be compressed for deployment, and then expanded later, without impairing the compression or expansion of the overall structure. Also, the weld must be compatible with both stent materials. Preferably, half the length of the Z stent single cylinder (1.5-5 cm) is projecting out of the top of the braided stent or Wallstent and the other half is deployed within the interior of the braided stent or Wallstent, thereby helping to constrain the Z stent from its full expansion and potentially eroding through the vein wall. The strong radial strength of the Z stent cylinder 21 corrects most of the structural deficiencies of the braided stent or Wallstent when located at the iliac-caval junction, as noted above. The other end of this combination stent would be the open bottom end of the braided stent or Wallstent. This combination will enable the modified stent to be deployed in one piece, reducing technical effort and cost and providing better positioning of the overall integrated stent structure.

A new sheath design may be necessary for deployment as the push-pin sheath used with standard Wallstents may not work satisfactorily. The deficiencies can be corrected by using a larger sheath with the current push delivery mechanism. The venous system easily tolerates sheaths up to 18 Fr. with ease and negligible access site problems. A biaxial or triaxial sheath mechanism may be necessary.

Figures 3, 4:
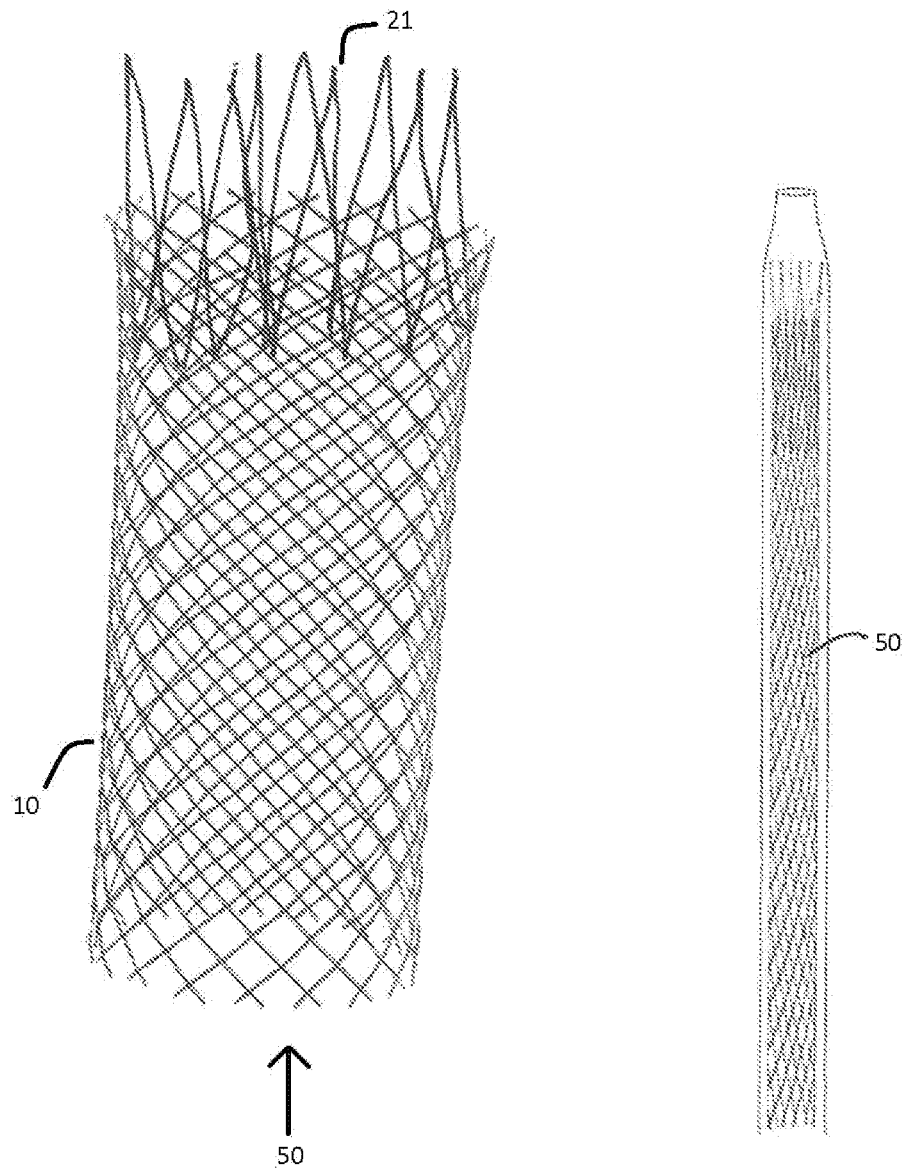
FIG. 3 is a top perspective view of a single cylinder Z stent inserted into the interior of a Wallstent with ½ the length of the Z stent extending above the end of the Wallstent, when both are expanded.
FIG. 4 is a front perspective view of the integrated Wall and Modified Z stent of FIG. 4 sheathed for deployment.

We recommend diameters of 20 mm, 18 mm, and 16 mm, with 9 cm and 6 cm lengths for the integrated stent deployment into the common iliac junction. These will typically be deployed in the common iliac vein. We also recommend 14 mm and 12 mm diameters in 6 cm and 4 cm lengths for the integrated stent for deployment into the external iliac and common femoral veins. The 14 mm length combination stent can be deployed in the external iliac vein with the Z stent cylinder 21 top striding across the internal iliac vein orifice, with the extended Z portion deployed in the standard Wallstents of existing design or other suitable braided stents and dimensions should still be available to incorporate the new design further if necessary. FIG. 4 shows the integrated stent system of FIG. 3 sheathed for deployment.

The radial expansion force of the Z stent cylinder 21 is greater than that of the braided stent or Wallstent. It is preferred that the braided stent or Wallstent constrain the Z stent, to avoid overexpansion of the Z stent portion of the system and possibly damaging the vein wall. It may be necessary to strengthen the terminating end of the Wallstent, for instance by using thicker braids at the terminating end to add radial resistance against the Z stent portion of the combination stent. Alternatively, a short stout stent or non-expansive sleeve, about 3 cm long, of the same diameter as the Wallstent, could be used external to the Wallstent terminal top end to provide the desired resistance to overexpansion of the Z stent cylinder 21 portion. Alternatively, the Z stent cylinder 21 could retain an expansive limiting band around the lower end (or both ends) to restrain Z stent cylinder 21 from full expansion. The band would have to survive the process of joining the two stents, such as by welding.

The end-to-end combined stent embodiment described above may be most useful to reinforce other choke points in the iliac vein system, such as inguinal ligament crossing. In this case one of the Wallstent stents in the stack would extend several centimeters past this choke point (for instance, a 14 mm Wallstent). An end-to-end combination stent would then be inserted several centimeters into the prior-placed Wallstent; the terminating single cylinder or double cylinder Z stent cylinder 21 portion deployed so that the terminating end of the combined stent containing the Z stent cylinder 21 portion in the end-to-end combination, is positioned next to the ligament crossing in order to reinforce this weak point.

In another embodiment, a single stent could be a laser cut, for instance from a nitinol, cylinder where the top of the cylinder is thicker than the remainder of the cylinder. The top should be more rigid and crush resistant and with large interstices, and the bottom would be laser cut so that the bottom end is very flexible to approximate the flexibility of a braided stent. The stent would be deployed with a portion of the more rigid top portion positioned in the vena cava proper.

The invention claimed is:

1. A combination of an expandable Z stent cylinder with a braided stent, where the Z stent cylinder has Z shaped struts formed in a wire with two ends, and the two ends of the wire being joined together forming a single closed cylinder having a first and a second open ends and a length L1 between the open ends, and a first diameter D1 when expanded; and an expandable braided stent, where the braids are spiral wound into a mesh pattern along the length of the braided stent, where the braided stent has a top open end and a bottom open end, and a length L2 between the braided stent open ends, where L2>L1, and a second diameter D2 when expanded, where a non-zero length L3 of the Z stent cylinder where 0<L3<L1 overlaps the braided stent adjacent to the top open end of the braided stent when both are expanded, to create an overlapped region between the two stents, where the overlapped length L3 of the Z stent cylinder is positioned either totally external or totally internal to the braided stent, and a non-zero remaining portion of the length of the Z stent cylinder that extends beyond the braided stent top open end when both are expanded, where the Z stent cylinder is fixedly joined to the braided stent in the overlapped region to create an integrated combination expandable stent.

2. The combination of claim 1 where a subset of the Z stent cylinder's Z shaped struts in the overlapped region are welded to a subset of the braided stent's braids.

3. The combination of claim 1 where the overlapped length L3 of the Z stent cylinder is positioned totally interior to the braided stent.

4. The combination of claim 3 where the braided stent acts as an exterior sleeve restricting the full expansion of the Z stent cylinder.

5. The combination of claim 1 where D1=20 mm and D2=18 mm.

6. The combination of claim 1 where the overlapped length L3 of the Z stent cylinder is approximately half the length of the Z stent cylinder.

\* \* \* \* \*